United States Patent
Schmieding et al.

(10) Patent No.: US 9,855,393 B2
(45) Date of Patent: Jan. 2, 2018

(54) DELIVERY NEEDLE WITH ELEVATOR/PADDLE FOR MICRONIZED ALLOGRAFT TISSUE

(71) Applicant: Arthrex, Inc., Naples, FL (US)

(72) Inventors: Reinhold Schmieding, Naples, FL (US); Brandon L. Roller, Naples, FL (US); Robert Benedict, Ft. Myers, FL (US); Marc Stoll, Ft. Myers, FL (US); James R. McWilliam, Rye, NY (US)

(73) Assignee: Arthrex, Inc., Naples, FL (US)

( * ) Notice: Subject to any disclaimer, the term of this patent is extended or adjusted under 35 U.S.C. 154(b) by 362 days.

(21) Appl. No.: 14/453,236

(22) Filed: Aug. 6, 2014

(65) Prior Publication Data

US 2015/0045768 A1 Feb. 12, 2015

Related U.S. Application Data

(60) Provisional application No. 61/863,346, filed on Aug. 7, 2013.

(51) Int. Cl.
| | |
|---|---|
| *A61M 31/00* | (2006.01) |
| *A61M 5/32* | (2006.01) |
| *A61L 27/36* | (2006.01) |
| *A61F 2/46* | (2006.01) |
| *A61B 17/88* | (2006.01) |
| *A61F 2/30* | (2006.01) |

(52) U.S. Cl.
CPC ......... *A61M 5/3286* (2013.01); *A61B 17/885* (2013.01); *A61B 17/8811* (2013.01); *A61F 2/4601* (2013.01); *A61F 2/4618* (2013.01); *A61L 27/3612* (2013.01); *A61M 5/3294* (2013.01); *A61F 2/30756* (2013.01); *A61F 2002/30588* (2013.01); *A61F 2002/4602* (2013.01)

(58) Field of Classification Search
CPC .. A61B 17/8811; A61F 2/4601; A61F 2/4618; A61M 5/3286; A61M 5/3294; A61M 35/003
See application file for complete search history.

(56) References Cited

U.S. PATENT DOCUMENTS

| | | | |
|---|---|---|---|
| 4,927,283 | A | 5/1990 | Fitjer |
| 2003/0050666 | A1 | 3/2003 | Grafton |
| 2009/0143819 | A1 | 6/2009 | D'Agostino |
| 2012/0029561 | A1 | 2/2012 | Olson |
| 2013/0158560 | A1 | 6/2013 | Gleason |
| 2013/0338792 | A1 | 12/2013 | Schmieding et al. |

FOREIGN PATENT DOCUMENTS

| | | |
|---|---|---|
| WO | WO-2006/125100 A1 | 11/2006 |
| WO | WO-2006/138300 A2 | 12/2006 |
| WO | WO-2012/151253 A1 | 11/2012 |

*Primary Examiner* — Rebecca E Eisenberg
(74) *Attorney, Agent, or Firm* — McDonnell Boehnen Hulbert & Berghoff LLP (57) ABSTRACT

Techniques, kits and a delivery instrument for providing a material at a defect repair site. The instrument is a combined delivery needle/elevator/paddle that includes a delivery needle and a paddle/elevator tip attached to the end of the needle and around the most distal opening of the needle. The combined needle/elevator/paddle instrument allows both delivery (insertion or injection) of the material/mixture as well as leveling/flattening of the delivered material. The mixture/material may be micronized allograft tissue such as BioCartilage® and the surgical site may be a defect site such as a microfracture site or cartilage defect.

29 Claims, 5 Drawing Sheets

DELIVERY NEEDLE WITH ELEVATOR/PADDLE FOR MICRONIZED ALLOGRAFT TISSUE

CROSS-REFERENCE TO RELATED APPLICATIONS

This application claims the benefit of U.S. Provisional Application No. 61/863,346, filed Aug. 7, 2013, the disclosure of which is incorporated by reference in its entirety herein.

FIELD OF THE INVENTION

The present invention relates to the field of surgery and, more particularly, to improved technologies for delivery of mixtures and materials over a surgical site.

BACKGROUND OF THE INVENTION

A recent technology used to augment microfracture techniques is through the use of an allograft extracellular matrix such as BioCartilage®, as detailed and disclosed in U.S. Patent Application Publication No. 2013/0338792, the disclosure of which is incorporated by reference in its entirety herewith. BioCartilage® is an example of desiccated micronized cartilage extracellular matrix tissue allograft that has been developed for ICRS grade III or greater articular cartilage lesions in conjunction with microfracture.

As detailed in US Patent Application Publication No. 2013/0338792, micronized allograft tissue (such as BioCartilage®) is delivered into a cartilage defect by injecting the micronized allograft tissue into the defect using a Tuohy designed needle, then removing the needle and putting a tamp or elevator/paddle to flatten down the micronized allograft tissue within the defect. If more material is needed within the defect, the tamp/elevator/paddle is removed and the Tuohy needle is inserted again for delivery of material.

A need exists for techniques that allow delivery of mixtures or materials such as micronized allograft tissue (for example, allograft cartilage tissue) over a surgical site with an instrument that also allows leveling of the delivered micronized allograft tissue, without the need to insert additional tamp/elevator/paddle instruments.

BRIEF SUMMARY OF THE INVENTION

The present invention provides techniques and delivery instrumentation for implantation of mixtures/materials such as micronized allograft tissue over a surgical site. The mixture (micronized allograft tissue) is delivered over a surgical site with a delivery needle provided with an elevator/paddle attached to the end of the needle and around the most distal opening of the needle. The combined needle/elevator/paddle instrument allows both delivery (insertion or injection) of the mixture (micronized allograft tissue) as well as leveling/flattening of the delivered material. Optionally, the combined needle/elevator/paddle instrument may be also employed in the preparation of the defect site, for example, removing damaged cartilage and forming vertical margins by using sharpened edges provided on the perimeter of the elevator/paddle attached to the end of the needle.

Other features and advantages of the present invention will become apparent from the following description of the invention.

DETAILED DESCRIPTION OF THE INVENTION

The present invention provides instruments and delivery techniques for providing a material or mixture over a surgical site. The hybrid instrument of the present invention is a combined delivery needle/elevator/paddle that includes a delivery needle and a paddle/elevator tip attached to the end of the needle and around the most distal opening of the needle. The combined needle/elevator/paddle instrument allows both delivery (insertion or injection) of the material/mixture as well as leveling/flattening of the delivered material. The combined needle/elevator/paddle instrument may be also employed in the actual defect site preparation, for example, in removing the damaged cartilage and forming vertical margins at the defect site (by using sharpened edges provided on the perimeter of the elevator/paddle attached to the end of the needle). In an exemplary embodiment, and as detailed below, the mixture/material may be micronized allograft tissue such as BioCartilage® and the surgical site may be a defect site such as a microfracture site or cartilage defect (for example, any articular cartilage surface defect of a knee, an ankle, a foot, a shoulder, a hand, a wrist, an elbow, or a hip, among others).

The present invention also provides methods of tissue repairs by providing/implanting a material/mixture over a surgical site. An exemplary tissue repair according to the present invention comprises inter alia the steps of: (i) providing a mixture having a paste-like consistency that can be dispensed through a needle or small cannula; and (ii) delivering the mixture at the defect site with a hybrid delivery needle/elevator/paddle instrument that allows both delivery of the mixture as well as flattening of the delivered mixture at the surgical site. If more material is needed within the defect, the hybrid delivery needle/elevator/paddle instrument is simply maintained at the defect site and more material/mixture is dispensed/delivered through the delivery needle of the hybrid instrument, without removing the instrument and without replacing the instrument with additional instrumentation.

Another exemplary tissue repair according to the present invention comprises inter alia the steps of: (i) preparing a surgical site by employing a hybrid delivery needle/elevator/paddle instrument with sharp edges (cutting edges) that allow removal of cartilage and formation of at least one vertical margin at the defect site; (ii) delivering a mixture (having a paste-like consistency that can be dispensed through a needle or small cannula) at the defect site by employing the hybrid delivery needle/elevator/paddle instrument; and (iii) flattening and leveling off the delivered mixture at the defect site by employing the elevator/paddle of the hybrid delivery needle/elevator/paddle instrument.

In an exemplary embodiment only, the mixture is a micronized allograft mixture which may be obtained by mixing allograft tissue (cartilage) micronized into particles with an autologous blood product (whole blood, platelet-rich plasma, autologous conditioned plasma, bone marrow, or stems cells, among others). In an exemplary embodiment only, the surgical site is a microfracture site of an articular cartilage defect.

Allograft cartilage tissue is delivered over a cartilage defect that has been debrided and microfractured, without the need for a periosteal covering or separate type of patch sewn over the top. The allograft tissue may be any micronized cartilage particulates obtained by various methods, for example, cartilage delivered in its native form, dehydrated via lyophilization, "freeze-dried," dehydrated via desiccation, or dehydrated by any other method.

As detailed below, the combined delivery needle/elevator/paddle instrument of the present invention provides the following improvements and benefits to the surgical technique of interest:

1. Delivery needle (Tuohy needle) with the elevator/paddle attached to the end of the Tuohy needle around the opening of the delivery needle.
2. The elevator/paddle portion may be curved so that the curvature will be tangential to the surface that the material is being applied. This curve allows the tangential aspect no matter what angle the needle is inserted toward the defect.
3. At the tip, there is a portion that extends way from the elevator/paddle that can function as a "bulldozer" when pushing forward and as a hoe/rake when pulling the material back toward the defect.
4. The handle around the proximal aspect of the needle allows the needle to be handled universally. It allows a person's hand to support the needle in a 360 degree fashion while using the thumb of the same hand to push the obturator and dispense the material through the needle.
5. A suction tip may be added to where the suction tube aligns next to the needle and has an opening that aligns next to the opening of the delivery needle. This can be used to aspirate blood immediately before addition of micronized allograft tissue (BioCartilage®) into the defect site.

Figure 7:
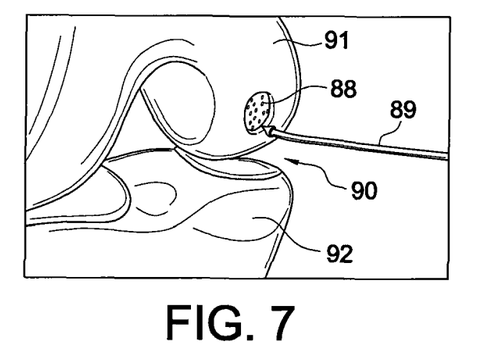
FIGS. 7-9 illustrate a method of delivering micronized allograft with the exemplary delivery needle with attached paddle/elevator of FIG. 1-6, and according to the present invention.
Figure 8:
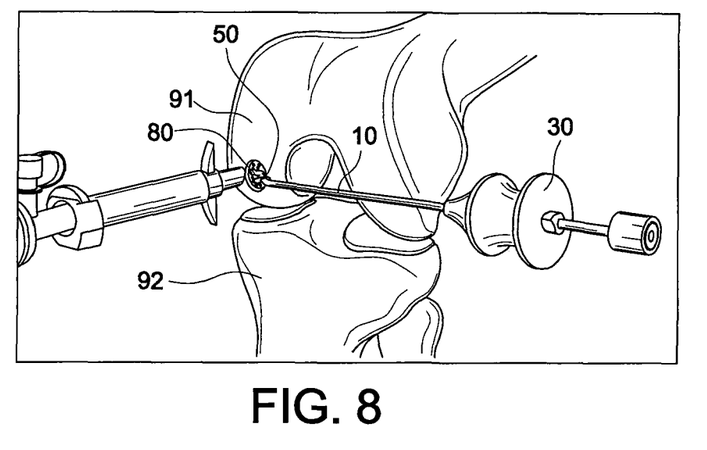
Figure 9:
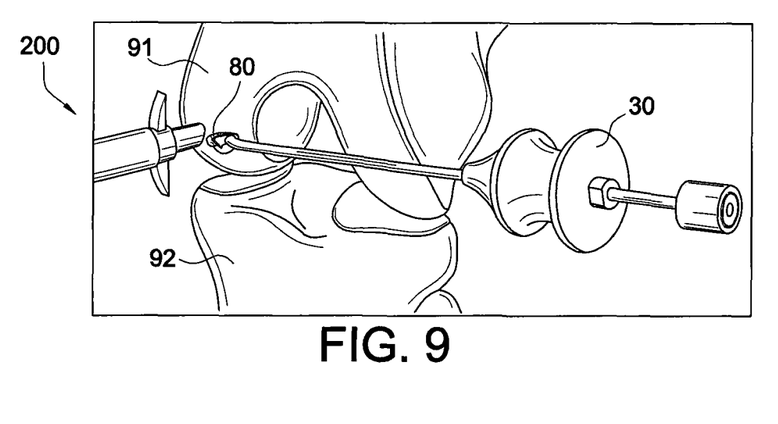
Figure 10:
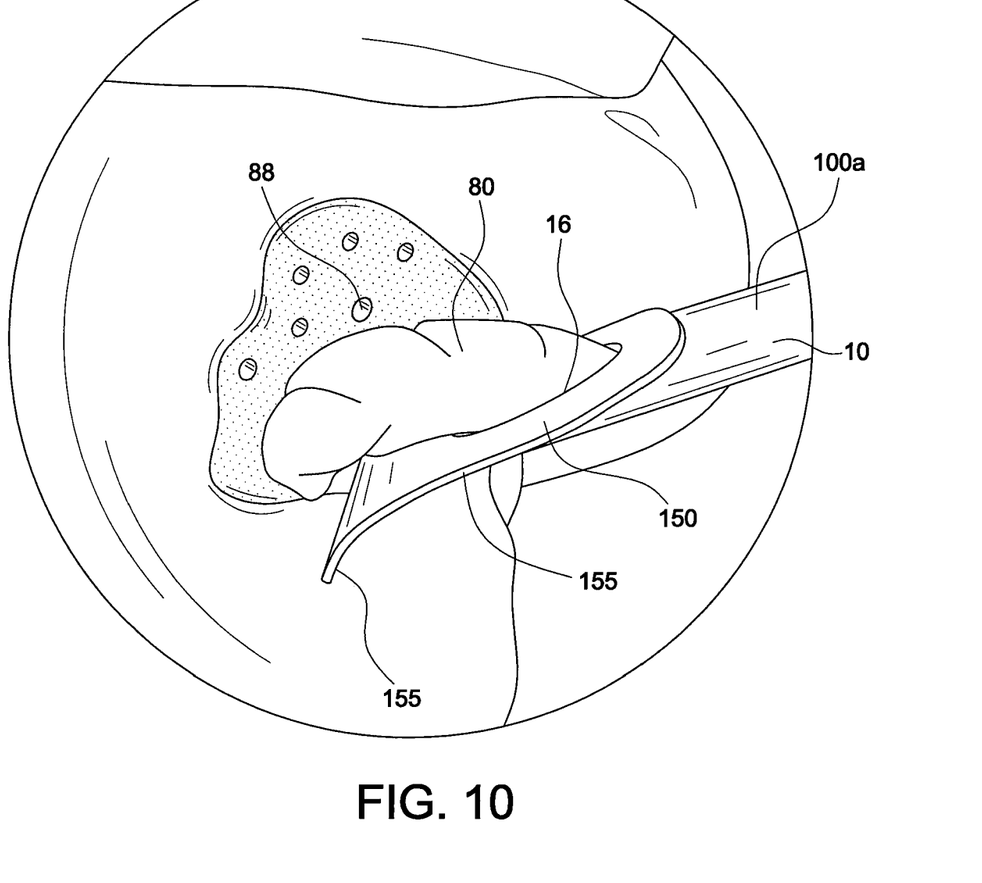
FIGS. 10 and 11 illustrate enlarged views of a distal end of another exemplary delivery needle with attached paddle/elevator of the present invention (with sharp edges that allow defect preparation) and provided at a microfracture site.
Figure 11:
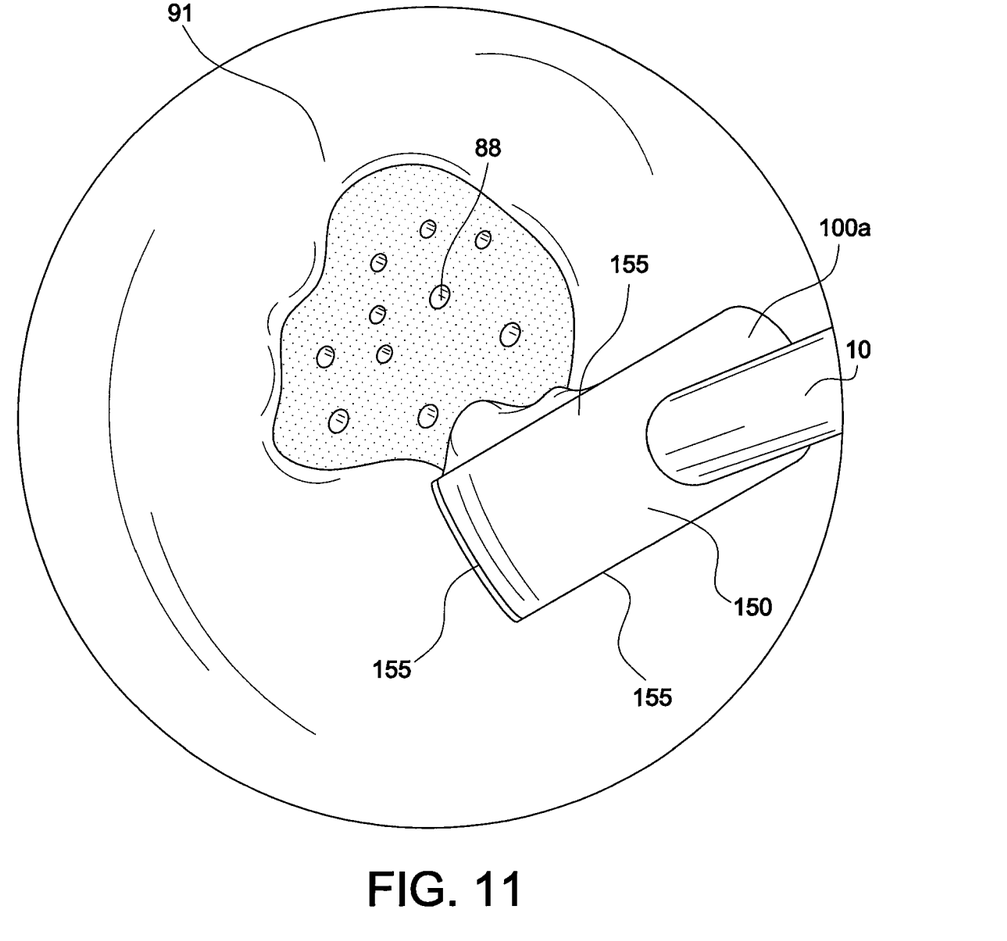

Referring now to the drawings, where like elements are designated by like reference numerals, FIGS. 1-6 illustrate various views of hybrid instrument 100 of the present invention which may be employed for the delivery and leveling/flattening of a mixture/material/composition having a paste-like consistency at a defect site. FIGS. 7-9 illustrate exemplary steps of a method of surgery employing hybrid instrument 100. FIGS. 10 and 11 illustrate another exemplary instrument 100a (delivery needle with attached paddle/elevator) of the present invention according with another embodiment, i.e., provided with sharp edges that allow defect site preparation.

Figure 1:
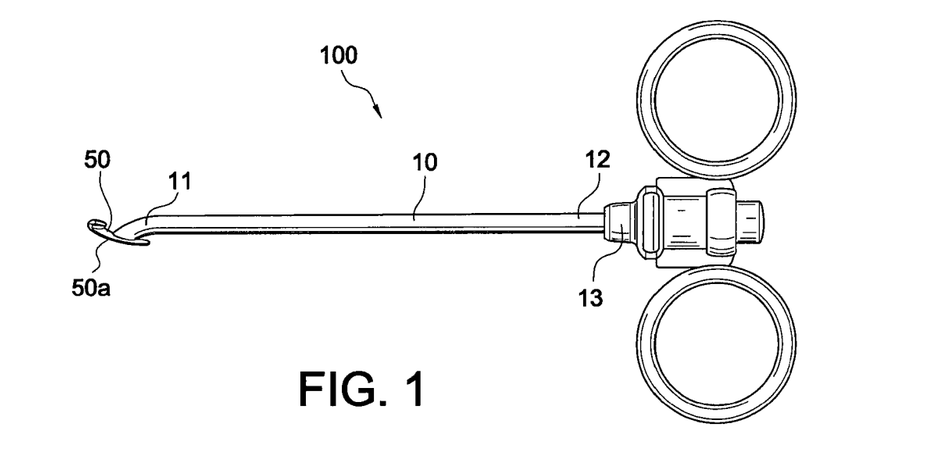
FIGS. 1-6 illustrate an exemplary delivery needle with attached paddle/elevator for delivering and leveling of a mixture (exemplary micronized allograft tissue) according to an exemplary embodiment of the present invention.
Figure 2:
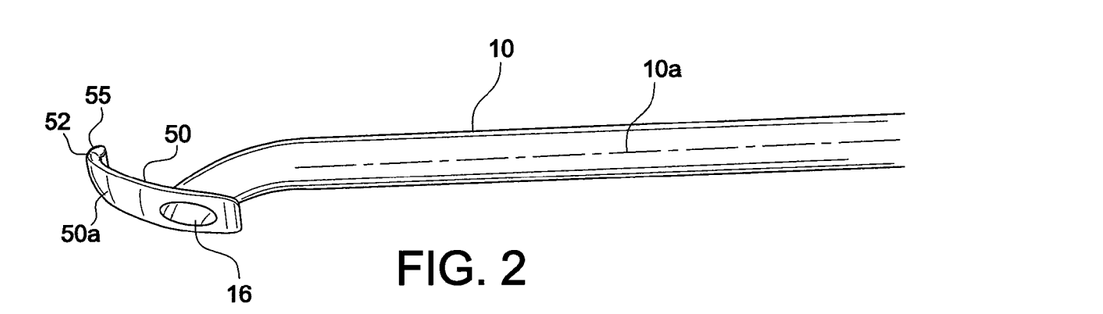
Figure 3:
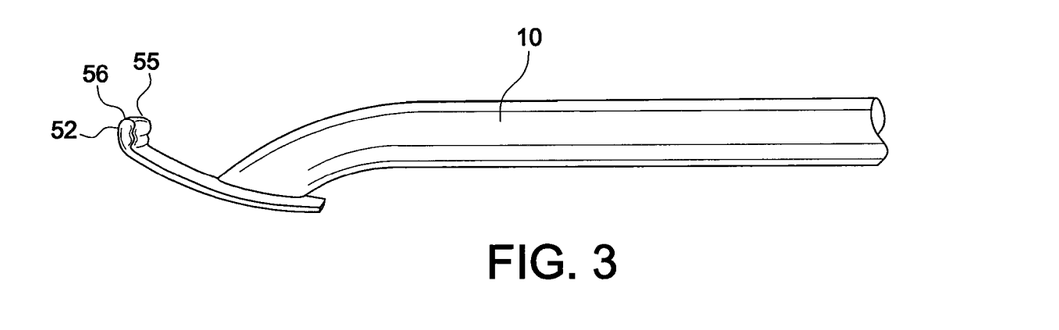

As illustrated in FIGS. 1-3, hybrid instrument 100 is formed of a delivery needle 10 and an elevator/paddle 50 (attachment 50 or paddle/elevator component 50) provided at a most distal end 11 of needle 10. Elevator/paddle 50 may be integral with the needle 10 or releasably attached to it, depending on the intended application. Preferably, the elevator/paddle 50 is integrally attached to the most distal end 11 of needle 10 and has a slightly curved configuration.

Figure 4:
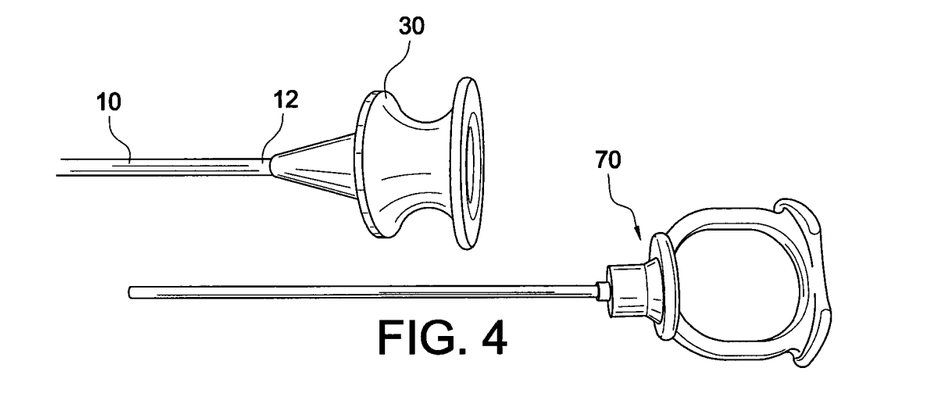
Figure 5:
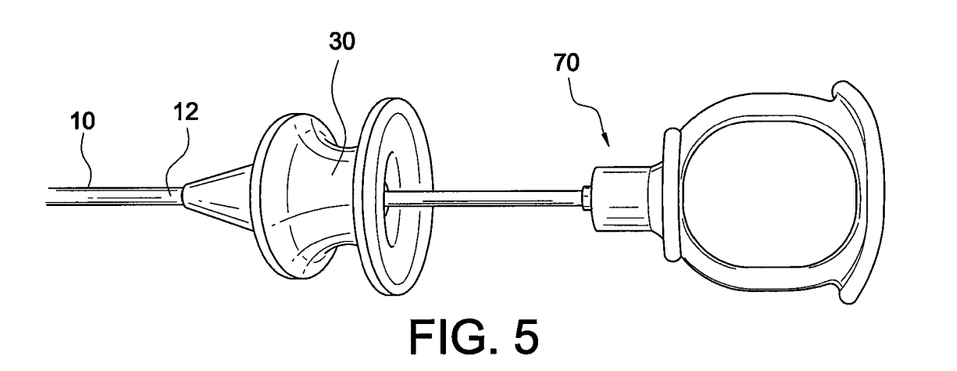
Figure 6:
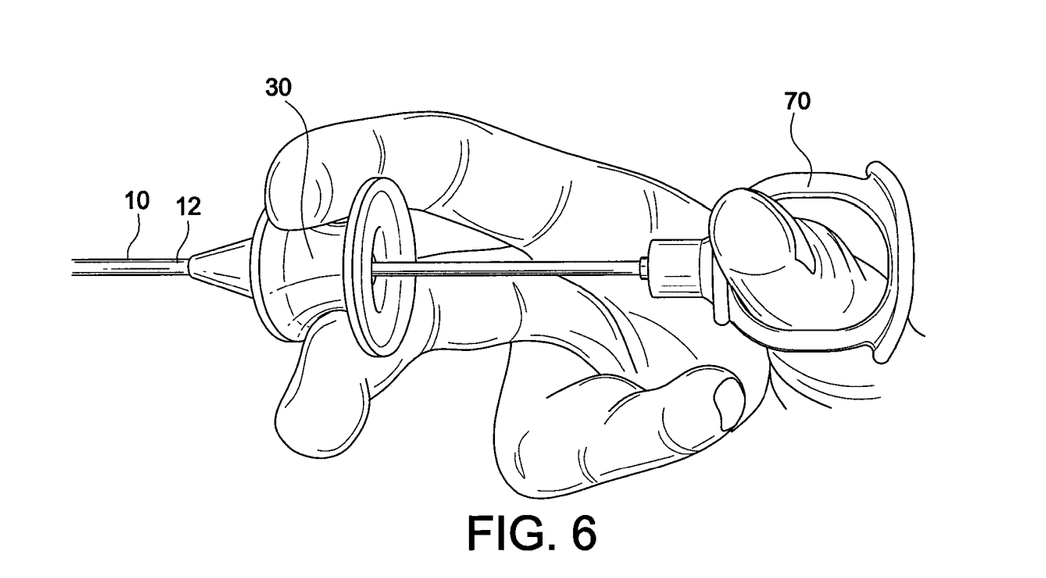

Delivery needle 10 has a substantially straight, tubular configuration with a longitudinal axis 10a, a distal end 11 attached to the curved elevator/paddle 50, and with a proximal end 12 attached to a hub 13 (for further engagement to a handle 30, shown in FIGS. 4-6). Distal end 11 has a substantially curved configuration to allow any injection of material to take place at an angle of insertion. Distal end 11 terminates in opening or aperture 16 (FIG. 2). In an exemplary embodiment, needle 10 is a Tuohy needle.

Paddle/elevator 50 is defined by a most distal surface 50a with a slight curve or curvature allowing to conform to each defect depending on the insertion angle of the device 100. The elevator/paddle portion 50 may be curved so that the curvature will be tangential to the surface that the material is being applied. This curve allows the tangential aspect no matter what angle the needle is inserted toward the defect.

A lip 55 is provided on top edge 52 of paddle/elevator 50 allowing the ability to push material forward or rotate the needle 10 about 180 degrees and to also use it to pull material back into the defect. Lip 55 extends away from the body of paddle/elevator 50 and functions as a "bulldozer" when pushing forward, and as a hoe/rake when pulling the material back towards the defect site. Top surface 56 of lip 55 is about at the same level with a top surface of the tubular member forming needle 10. The paddle/elevator 50 is attached to the end of the delivery needle 10 around the opening 16 of the delivery needle 10.

Once the material has been provided at the repair site (i.e., injected at the repair site and/or dispensed with an obturator), the paddle 50 is used to flatten the material over the defect. FIG. 3 illustrates in more detail the curved profile of the paddle/elevator allowing to conform to each defect depending on the insertion angle of the device. The lip 55 allows the user to push the material forward or to rotate the needle 10 about 180 degrees and then use it to pull the material back into the defect.

FIGS. 4-6 illustrate an obturator 70 used with instrument 100 to dispense the material out of the needle 10. As noted above, as the material is dispensed, the paddle/elevator 50 can be used to flatten the material into the defect. Handle 30 for the needle 10 (attached at proximal end 12 of the needle 10) conforms to two fingers holding the needle 10 in a 360 degree fashion (as shown in FIG. 6) and provides flexibility on where to support the needle when working to push the obturator 70 and inject the material.

Instrument 100 described above may be provided as part of a kit that may be a simple delivery kit which includes additional instruments for delivery of material 80 (for example, micronized allograft tissue mixtures having a paste-like consistency) to be provided/delivered over a defect site, for example, over a microfractured defect.

The kit may be also a mixing and delivery kit which may further include at least one mixing syringe and additional needles (which may be curved needles such as Tuohy delivery needles or straight needles), and one or more obturators such as obturator 70, for example, to aid in the delivery of the micronized allograft mixture at the defect site. A funnel may be also optionally included as part of the mixing and delivery kit.

FIGS. 7-9 illustrate an exemplary method of delivering material 80 (micronized allograft or mixture) over an exemplary microfractured defect with the hybrid instrument 100 of the present invention.

FIG. 7 illustrates femur 91, tibia 92 and surgical site 90 containing an articular cartilage defect to be repaired with the instrument 100 of the present invention and by a surgical method according to the present invention.

FIG. 7: Debride the articular cartilage defect 90 to a stable border with about perpendicular margins. A scalpel or cutting instrument may be used to create the vertical margins and a curette can be used to debride the calcified cartilage layer at the base of the defect. When evaluating a cartilage defect and preparing it, care must be taken to debride the cartilage to a healthy cartilaginous border. In addition, 90° margins should be created around the periphery of the defect to help with containment of the product.

Bone marrow stimulation is conducted using standard microfracture surgery to form several perforations in the subchondral bone plate of microfracture site 88. A power pick 89 (FIG. 7) may be used to perform this procedure while applying irrigation fluid to avoid thermal necrosis. The microfracture procedure is performed through the subchondral plate which allows marrow elements to incorporate into the implanted allograft material.

Before implanting material 80, a drop or two of fibrin adhesive may be optionally applied to the corners of the base of the defect to provide additional adhesive properties between the bone bed and allograft material.

Material 80 may include allograft cartilage which is micronized into particles with a small enough size (of about 0-300 microns) so that when it is mixed with a fluid (such as an autologous blood product) it has a paste-like consistency that can be injected through needle 10 of instrument 100. The autologous blood product may be blood (whole blood), autologous conditioned plasma, platelet-rich plasma, bone marrow (for example, bone marrow concentrate or bone marrow aspirate), stem cells (concentrated or expanded stem cells), or combinations thereof. The allograft cartilage can be provided in a dehydrated state via a desiccation process or hypothermic dehydration process instead of lyophilization of the material.

Material 80 may consist of micronized allograft mixture or cartilage paste formed by mixing the micronized cartilage tissue with the autologous blood solution. Material 80 is applied at the defect site 88 through delivery needle 10 of delivery system/instrument 100, as shown in FIG. 8. The paddle/elevator 50 of instrument 100 is then used to flatten/smooth out the material 80 over the defect 88. The lip 55 allows the surgeon to push the material 80 forward or to rotate the needle 10 about 180 degrees and use it to pull the material back into the defect.

Optionally, a light layer of fibrin or similar material may be applied over the mixture 80. The knee may be gently ranged before closure to assure cartilage mixture 80 adherence and completion of surgery and final repair 200 (FIG. 9).

In yet another embodiment, the hybrid instrument of the present invention may be also employed in the preparation of the defect site (repair site) preferably before the application/delivery of the material/mixture 80 and the flattening/leveling of such delivered material. For example, FIGS. 10 and 11 illustrate exemplary instrument 100a (delivery needle with attached paddle/elevator) of the present invention which is about similar to the instrument 100 detailed above, but differs from it in that instrument 100a is provided with a paddle/elevator 150 that has at least one sharp (sharpened) edge 155 that allow cutting/removal of tissue at the defect site and formation of at least one vertical margin defining the defect site.

For example, for a microfracture site preparation, the instrument 100a provides means for removing the damaged cartilage at defect site 88 by creating at least one vertical margin using the sharpened edges 155. Preferably, the paddle/elevator 150 is provided with multiple cutting sharpened edges 155 (for example, surrounding/provided on the perimeter of the paddle 150) to aid the surgeon in the cutting and removal of soft tissue, cartilage and/or bone at the defect site. In this manner, hybrid instrument 100a is employed for (i) preparing the defect site; (ii) delivering of the material/mixture at the prepared defect site; and (iii) leveling off/flattening the delivered material/mixture at the defect site, all steps being conducted with a same, single instrument 100a.

The material/mixture/composition 80 to be delivered and subsequently handled with the instrument 100, 100a of the present invention may be allograft tissue such as allograft cartilage in the form of micronized cartilage particulates which may be cartilage delivered in its native form, dehydrated via lyophilization, "freeze-dried," dehydrated via desiccation, or dehydrated by any other method, among others. The size of the particles forming the mixture allows the micronized particles to mix well with the autologous blood product and form the resulting mixture/paste.

In an exemplary-only embodiment, the material/mixture 80 may consist of BioCartilage®, sold by Arthrex, Inc. (Naples, Fla.), which consists essentially of allograft cartilage that has been dehydrated and micronized. BioCartilage®) contains the extracellular matrix that is native to articular cartilage including key components such as type II collagen, proteoglycans, and additional cartilaginous growth factors. The principle of BioCartilage® is to serve as a scaffold over a defect providing a tissue network that can potentially signal autologous cellular interactions and improve the degree and quality of tissue healing within a properly prepared cartilage defect.

Cartilage (in the form of morsellized, freeze-dried and/or desiccated cartilage) may be processed by a tissue bank similar to the BioCartilage® process for hyaline cartilage. The sterile, freeze-dried and/or desiccated product is mixed (by the orthopedic surgeon, for example) at the time of surgery with autologous blood or a biologic equivalent, to create a moldable allograft paste that can be delivered with instrument 100 at a surgical site.

The surgical site may be a microfracture site which may be part of any articular cartilage surface, for example, a knee, an ankle, a foot, a shoulder, a hand, a wrist, an elbow, or a hip, among others.

The mixtures/materials of the present invention (such as micronized cartilage mixture) may optionally comprise additional components such as proteins, growth factors or chemicals that may be provided within the mixtures. The autologous blood product may be blood (whole blood), plasma, autologous conditioned plasma, platelet-rich plasma, bone marrow, bone marrow aspirate, bone marrow concentrate, stem cells such as concentrated or expanded stem cells (derived from a variety of sources), or any combinations of these products.

In accordance with exemplary-only embodiments, the mixtures may be obtained to additionally comprise components such as growth factors, additional antiseptic chemicals and/or antibiotics and/or electrolytes, or hormones or site-specific hybrid proteins (that promote or enhance the wound healing effectiveness of the growth factors), or glue such as fibrin glue and/or adhesives, among others.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:
1. A surgical instrument for treatment of a defect site, comprising:
    a delivery needle configured to deliver a material, comprising a tubular portion with a longitudinal axis, a proximal end and a curved distal end;

a paddle integrally attached to the curved distal end, the paddle having a curved configuration and terminating in a lip at its most distal edge, the paddle being oriented at an angle relative to both the tubular portion and to the curved distal end of the delivery needle and wherein the delivery needle terminates at an opening or aperture in the paddle.

2. The surgical instrument of claim 1, wherein the delivery needle allows dispensing of a material at the defect site and the paddle allows leveling off the dispensed material at the defect site.

3. The surgical instrument of claim 2, wherein the paddle is provided with at least one sharp edge that is configured to cut and remove cartilage at the defect site.

4. The surgical instrument of claim 1, wherein the needle, the handle and the paddle are all integrally attached to each other.

5. The surgical instrument of claim 1, wherein the material is a biological allograft mixture consisting essentially of morselized, freeze-dried or desiccated cartilage and an autologous blood product.

6. The surgical instrument of claim 5, wherein the autologous blood product is blood, platelet-rich plasma, autologous conditioned plasma, bone marrow aspirate, bone marrow concentrate, stem cells, or combinations thereof.

7. The surgical instrument of claim 1, wherein the defect site is a microfracture site which is part of a cartilage surface.

8. The surgical instrument of claim 7, wherein the cartilage surface is part of a knee, an ankle, a foot, a shoulder, a hand, a wrist, an elbow, or a hip.

9. A method of surgery comprising the steps of:
providing the surgical instrument of claim 1 in the vicinity of a defect site; and
delivering a material at the defect site with the surgical instrument and flattening the delivered material with the surgical instrument.

10. The method of claim 9, further comprising the step of dispensing the material at the defect site by employing an obturator.

11. The method of claim 9, further comprising the step of removing tissue at the defect site with the surgical instrument and forming at least one vertical margin at the defect site.

12. The method of claim 9, wherein the surgical instrument comprises a delivery needle and a paddle integral with a most distal end of the delivery needle, the paddle having a substantially curved configuration and terminating in a lip at its most distal end.

13. The method of claim 9, wherein the defect site is a microfracture site and the method further comprises the step of conducting microfracture surgery to obtain the microfracture site.

14. The method of claim 9, wherein the material is a micronized allograft mixture comprising micronized allograft tissue particles and an autologous blood product.

15. The method of claim 14, wherein the micronized allograft tissue particles have a size of about 0-300 microns.

16. The method of claim 14, wherein the micronized allograft tissue particles are desiccated cartilage particles.

17. The method of claim 14, wherein the micronized allograft mixture consists essentially of micronized allograft tissue particles and autologous blood product.

18. The method of claim 14, wherein the autologous blood product is selected from the group consisting of whole blood, autologous conditioned plasma, platelet-rich plasma, bone marrow aspirate, bone marrow concentrate, and stem cells.

19. The method of claim 9, wherein the defect site is part of a cartilage surface.

20. The method of claim 19, wherein the defect site is part of a knee, an ankle, a foot, a shoulder, a hand, a wrist, an elbow, or a hip.

21. A method of articular cartilage repair, comprising the steps of:
preparing a cartilage defect by microfracture surgery;
preparing a micronized cartilage paste with particles size of about 0-300 microns, the micronized cartilage paste consisting essentially of micronized cartilage particulates and autologous blood product; and
applying the micronized cartilage paste over the cartilage defect without the need of applying a covering over the cartilage defect and by employing the surgical instrument of claim 1, the surgical instrument allowing both delivery of the micronized cartilage paste over the cartilage defect and leveling of the delivered micronized cartilage paste.

22. The method of claim 21, wherein the micronized cartilage particulates are obtained by dehydration of cartilage via desiccation.

23. The method of claim 21, wherein the micronized cartilage particulates are obtained by dehydration of cartilage via desiccation or lyophilization.

24. The method of claim 21, further comprising the step of adding, to the micronized cartilage paste, a component selected from the group consisting of growth factors, antiseptics, antibiotics, electrolytes and stem cells.

25. The method of claim 21, further comprising the step of removing cartilage at the cartilage defect by employing sharpened edges of the combined needle/paddle instrument.

26. A kit for delivering a micronized allograft paste to repair a microfracture site of a cartilage defect, comprising:
a hybrid delivery needle/elevator/paddle instrument comprising a tubular delivery needle, with a curved end and a straight end, a paddle or elevator component integrally attached to the curved end, and a handle attached to the straight end; and
an obturator.

27. The kit of claim 26, further comprising a mixing syringe for mixing micronized allograft particles with an autologous blood product to form the micronized allograft paste.

28. The kit of claim 26, wherein the paddle or elevator component is provided at the end of the curved end and around an opening of the curved end of the delivery needle.

29. The kit of claim 26, wherein the paddle or elevator component is provided with at least one sharpened edge that cuts and removes cartilage or bone.

* * * * *

UNITED STATES PATENT AND TRADEMARK OFFICE
CERTIFICATE OF CORRECTION

PATENT NO. : 9,855,393 B2  Page 1 of 1
APPLICATION NO. : 14/453236
DATED : January 2, 2018
INVENTOR(S) : Schmieding et al.

It is certified that error appears in the above-identified patent and that said Letters Patent is hereby corrected as shown below:

In the Claims

Column 6, Line 67, insert -- a handle attached at the proximal end; and --

Column 8, Line 41, delete "combined needle/paddle", insert -- surgical --

Signed and Sealed this
Tenth Day of July, 2018

Andrei Iancu
*Director of the United States Patent and Trademark Office*